(12) United States Patent
Markovitch (10) Patent No.: US 8,939,287 B2
(45) Date of Patent: Jan. 27, 2015

(54) STORAGE DEVICE

(75) Inventor: Daniel Andrew Markovitch, Chesterfield (GB)

(73) Assignee: INOV8 Medical Solutions Limited, Chersterfield, Derbyshire (GB)

( * ) Notice: Subject to any disclaimer, the term of this patent is extended or adjusted under 35 U.S.C. 154(b) by 0 days.

(21) Appl. No.: 13/881,003

(22) PCT Filed: Jul. 14, 2011

(86) PCT No.: PCT/GB2011/051324
§ 371 (c)(1),
(2), (4) Date: May 17, 2013

(87) PCT Pub. No.: WO2012/056206
PCT Pub. Date: May 3, 2012

(65) Prior Publication Data
US 2013/0220855 A1     Aug. 29, 2013

(30) Foreign Application Priority Data

Oct. 27, 2010 (GB) .................................. 1018179.0
Jun. 7, 2011 (GB) .................................. 1109522.1

(51) Int. Cl.
*A61L 2/00*     (2006.01)
*A61B 19/02*     (2006.01)
*A61L 2/26*     (2006.01)

(52) U.S. Cl.
CPC ........... *A61B 19/026* (2013.01); *A61B 19/0287* (2013.01); *A61L 2/26* (2013.01);
(Continued)

(58) Field of Classification Search
USPC .......... 206/363, 807, 1.5; 220/4.21, 375, 827, 220/829
See application file for complete search history.

(56) References Cited

U.S. PATENT DOCUMENTS 3,485,416 A * 12/1969 Fohrman .................... 222/142.1
4,331,257 A     5/1982 Taschner
(Continued)

FOREIGN PATENT DOCUMENTS

DE    20 2010 005089 U1    8/2010
GB    2 261 359    5/1993
(Continued)

OTHER PUBLICATIONS

GB Search Report bearing a mailing date of Jan. 19, 2011, 1 page.
(Continued)

*Primary Examiner* — Steven A. Reynolds
*Assistant Examiner* — King M Chu
(74) *Attorney, Agent, or Firm* — Burr & Brown, PLLC (57) ABSTRACT

The present invention relates to a device for storage of medical equipment. In particular, the present invention relates to a single-use storage device for components of a piece of medical equipment that retains the components with the piece of medical equipment. More particularly the storage device may be used to store endoscope valves, with the parent flexible endoscope. A single-use storage device for medical equipment comprises a container portion, for holding one or more pieces of medical equipment, a closure portion, designed to engage with the container portion to form an enclosure around said medical equipment, a plurality of apertures permitting fluid flow through the storage device, and securing means to secure the closure portion to the container portion, the securing means arranged such that once the closure portion has been secured to the container portion using the securing means the closure portion and container portion cannot be separated without permanently disabling the securing means.

17 Claims, 7 Drawing Sheets

(52) U.S. Cl.
CPC .... *A61B 19/0256* (2013.01); *A61B 2019/0202* (2013.01); *A61B 2019/0211* (2013.01); *A61B 2019/0245* (2013.01); *A61L 2202/182* (2013.01); *A61L 2202/24* (2013.01)
USPC .......................................... 206/363; 220/4.21

(56) References Cited

U.S. PATENT DOCUMENTS

| | | | |
|---|---|---|---|
| 4,418,819 A * | 12/1983 | Shapiro | 206/216 |
| 4,658,955 A * | 4/1987 | Eichner | 206/307 |
| 4,782,977 A * | 11/1988 | Watanabe et al. | 220/324 |
| 5,031,768 A | 7/1991 | Fischer | |
| 5,044,512 A * | 9/1991 | Giancaspro et al. | 220/709 |
| 5,096,114 A | 3/1992 | Higginbotham | |
| 5,235,795 A | 8/1993 | DeBusk | |
| 5,285,918 A * | 2/1994 | Weisburn et al. | 220/265 |
| 5,294,413 A * | 3/1994 | Riihimaki et al. | 422/297 |
| 5,312,011 A * | 5/1994 | Fischer | 220/528 |
| 5,465,901 A * | 11/1995 | Paine, Jr. | 229/407 |
| 5,482,067 A | 1/1996 | Wittrock et al. | |
| 5,588,853 A * | 12/1996 | Anthony | 439/136 |
| 5,979,690 A * | 11/1999 | Hartley | 220/266 |
| 6,227,399 B1 | 5/2001 | Angus et al. | 220/375 |
| 6,699,331 B1 * | 3/2004 | Kritzler | 134/8 |
| 6,845,878 B2 | 1/2005 | Hayes et al. | 220/839 |
| 7,100,788 B2 * | 9/2006 | Cadiente et al. | 220/366.1 |
| 8,328,039 B2 * | 12/2012 | Short et al. | 220/324 |
| 2002/0162838 A1 * | 11/2002 | Leaphart et al. | 220/4.21 |
| 2003/0052133 A1 * | 3/2003 | Hayes et al. | 220/835 |
| 2003/0080571 A1 | 5/2003 | Schainholz et al. | |
| 2003/0198714 A1 * | 10/2003 | Cadiente et al. | 426/106 |
| 2004/0112896 A1 * | 6/2004 | Lewis | 220/212 |
| 2005/0139599 A1 | 6/2005 | Schainholz et al. | |
| 2005/0161355 A1 | 7/2005 | Matthis et al. | |
| 2006/0076309 A1 * | 4/2006 | Delman et al. | 215/306 |
| 2006/0266666 A1 | 11/2006 | Bettenhausen et al. | |
| 2006/0289549 A1 * | 12/2006 | Vovan | 220/791 |
| 2007/0045317 A1 * | 3/2007 | Rosender et al. | 220/266 |
| 2007/0138180 A1 * | 6/2007 | Vovan | 220/266 |
| 2007/0144926 A1 | 6/2007 | Bettenhausen et al. | |
| 2007/0212277 A1 * | 9/2007 | Riley | 422/292 |
| 2007/0272688 A1 * | 11/2007 | Longo et al. | 220/4.23 |
| 2008/0116095 A1 * | 5/2008 | Riley et al. | 206/363 |
| 2010/0127010 A1 * | 5/2010 | Short et al. | 220/781 |
| 2010/0158751 A1 | 6/2010 | Friderich et al. | |

FOREIGN PATENT DOCUMENTS

| | | |
|---|---|---|
| GB | 2 475 948 | 6/2011 |
| WO | 2004/018305 | 3/2004 |
| WO | 2005/053597 A2 | 6/2005 |
| WO | 2006/127230 A2 | 11/2006 |

OTHER PUBLICATIONS

GB Search Report bearing a mailing date of Sep. 26, 2011, 1 page.
Ruhof Endo-Bag Data Sheet and Article, www.rahol.co.uk. Sep. 15, 2011, 2 pages.
Partners for Endoscopy, www.plemedical.co.uk, Feb. 2009, 3 pages.
Abstracts from ESGENA Conference 2007, 11th Meeting of the European Society of Gastroenterology and Endoscopy Nurses and Associates, Oct. 27-29, 2007, 53 pages.
NHS Decontamination Standards for Flexible Endoscopes, National Endoscopy Programme, www.grs.nhs.uk, Mar. 2008, 14 pages.
Decontamination of Endoscopes, Medical Devices Agency, MDA DB2002(05), Jul. 2002, 55 pages.
The Report of an Independent Review of Endoscope Decontamination in Northern Ireland, Departement of Health, Ref: 296/2004, Mar. 2005, 52 pages.

* cited by examiner

STORAGE DEVICE

BACKGROUND a. Field of the Invention

The present invention relates to a device for storage of medical equipment. In particular, the present invention relates to a single-use storage device for components of a piece of medical equipment that retains the components with the piece of medical equipment. More particularly the storage device may be used to store endoscope valves, with the parent flexible endoscope.

b. Related Art

Flexible medical endoscopes are used for the internal examination of various parts of the human or animal body. They are produced in diameters ranging from 0.02 to 0.6 inches (0.5 to 15 mm) and with lengths of 12 to 120 inches (300 to 3000 mm). The majority of endoscopes have internal channels, down which air, water or accessories may be directed so as to facilitate examinations, or to carry out surgical procedures. Each of these channels typically includes one or more valves used to restrict and/or direct the flow of fluids or air, or allow the passage of instruments through the endoscope. The valves typically include a suction valve, an air/water valve, a biopsy valve and a cleaning valve.

Due to the invasive nature of many of the procedures for which flexible medical endoscopes are used, it is necessary that the endoscopes and all the detachable parts and components such as the valves are thoroughly cleaned and disinfected prior to and after each use. Typically endoscopes undergo a manual cleaning procedure before undergoing disinfection and sterilisation procedures.

At least in the United Kingdom and France, the recent BSE (Bovine Spongiform Encephalopathy) crisis has led to heightened concerns that the human form, Creutzfeldt-Jakob Disease (CJD), may be transmitted by contaminated endoscopes or their detachable parts. Moreover, the recent re-emergence of tuberculosis also presents a threat of airborne contamination in areas where endoscopes are being used and transported.

Ideally, the room in which the cleaning and disinfection of the endoscopes are carried out should be in fairly close proximity to the operating theatre or procedure room where the endoscope will be used, to avoid or minimise contamination between these areas. Furthermore, to reduce the possibility of cross-contamination and to allow accurate records to be kept regarding use of the endoscopes and the cleaning and sterilising procedures, all detachable parts of an endoscope should be kept with the parent scope for their entire service life.

At least two Guidelines regarding the use, storage and cleaning of endoscopes have recently been published. These state that endoscope valves and other detachable components should always remain as a unique set with the parent endoscope. The National Endoscopy Programme (UK) in its Decontamination Standards for Flexible Endoscopes states that: "Reusable valves should be decontaminated . . . and processed with their corresponding endoscope" and "Valves including flushing valves and removable parts are [to be] kept with the endoscope to form a unique set of equipment."

In addition, the European Society for Gastrointestinal Endoscopy (ESGE) guidelines states that: "Valves should be disconnected as they may block the air flow through the endoscope channels. Valves and distal caps should be stored separately but with the endoscope. Valves (including rinsing valves) should stay with a named endoscope as a set, to prevent cross-infection and enable full traceability."

It is therefore clear that valves and other detachable components must be fully removed from the endoscope, but should be kept with their unique parent endoscope. For example valves cannot be kept plugged into their endoscope ports but must remain with the endoscope. Existing methods of keeping endoscope valves with their parent endoscope vary between different countries and, notwithstanding the above guidance, these existing methods are generally considered unsatisfactory when based on such criteria as:

the protection of the endoscope valves before, during and after the processing of the endoscope and valves, either manually or in an automated endoscope reprocessor (AER), against accidental damage or contamination;

the protection of the staff, patients, and workplace against contamination and possible infection. The risk of contamination deriving from a used and potentially unclean set of endoscope valves due to either the use of non-dedicated cages to store the valves which have a small mesh thus not allowing disinfection solution through, or the use of non-dedicated material bags to store the valves which soak up liquid and can themselves potentially become a biohazard; and the protection of unused endoscopes against the potential for cross-contamination from contact with used endoscope valves carrying infectious matter.

It is an object of the present invention to provide a device that addresses the above-stated problems associated with keeping endoscope valves with their parent endoscope during cleaning and storage.

SUMMARY OF THE INVENTION

According to the invention there is provided a single-use storage device for medical equipment, the storage device comprising:

a container portion, for holding one or more pieces of medical equipment;

a closure portion, designed to engage with the container portion to form an enclosure around said medical equipment;

a plurality of apertures permitting fluid flow through the storage device; and securing means to secure the closure portion to the container portion, the securing means arranged such that once the closure portion has been secured to the container portion using the securing means the closure portion and container portion cannot be separated without permanently disabling the securing means.

As such, the present invention provides a single use storage device that allows valves and other components to be kept with a parent endoscope or other piece of medical equipment during storage, cleaning and sterilisation. In particular, the storage device may be used in hospitals for the storage of flexible medical endoscope valves together with their parent endoscope to ensure that they remain a unique set, before, during and after being processed in an automated reprocessing machine or by manual endoscope reprocessing.

Preferably the storage device further comprises a connecting portion joining the container portion to the closure portion. This connecting portion will typically be arranged such that there is a distinct separation of the container portion and closure portion. Preferably the device comprises a flexible connecting portion joining the container portion to the closure portion. The connection portion is arranged such that, when the closure portion is engaged with the container portion the connection portion forms a loop. Preferably the connection portion comprises a flexible strap which may be bent or looped around an object, such as an endoscope, when the storage device is closed so that the storage device is retained with the object.

In preferred embodiments the connection portion includes one or more protrusions on a first surface. These are provided so that contact between the connection portion and the object to which the storage device is attached is minimised. For example, a strap connecting the container portion to the closure portion may include raised projections to minimise the contact of the strap with a parent endoscope umbilical (light-guide) cable around which the strap is looped.

To enable a sufficient flow of fluid through the device it is desirable to include a plurality of apertures in both the container portion and the closure portion. Typically the apertures will comprise holes through the base and/or walls of the container portion and closure portion.

Preferably a first part of the securing means is provided in the container portion and a second part of the securing means in provided in the closure portion. In some embodiments, the securing means comprises an opening the container portion and a protrusion in the closure portion, and wherein a part of the protrusion is passed through the opening to secure the closure portion to the container portion. The securing means may comprise more than one opening and more than one protrusion.

Because the storage device is designed to be used only once, to minimise contamination of medical equipment for example, it is preferable to design the securing means so that disabling the securing means includes breaking a part of the securing means. To allow a user to easily break open the storage device, it is preferable if the closure portion includes a handle portion. The handle portion is arranged to enable a user to grip the handle to separate the closure portion from the container portion, thereby disabling or breaking the securing means.

To enable more than one component to be held securely within the storage device, the container portion may include a partitioning member, which divides at least a part of the volume of the container portion into discrete regions.

In preferred embodiments of the invention the closure portion is a lid.

The container portion may comprise a tray compartment. In embodiments in which the container portion is a tray compartment, the closure portion is preferably in the form of a sleeve, and the tray compartment is receivable within the sleeve. Preferably the tray compartment and sleeve are substantially rectangular in shape and are arranged such that the tray compartment is received completely within the sleeve to form a substantially rectangular box, or cage.

In embodiments comprising a tray and a sleeve, preferably a first part of the securing means is provided on the tray compartment and a second part of the securing means is provided on the sleeve. In some embodiments it may be preferable if the first and second parts of the securing means comprise a plurality of semi-dome protrusions arranged such that when the tray compartment is engaged with the sleeve, flat surfaces of the protrusions interlock to prevent disengagement of the tray compartment from the sleeve.

Preferably the container portion and closure portion are formed from a plastics material. The material from which the storage device is made should, ideally, be resistant to all modern cleaning chemicals.

Preferably the storage device comprises further apertures or grooves that enable chains, ties or similar to pass outside of the device so that, for example, instruction cards or labels that are connected to the valves via the chains or ties can be kept outside the device.

BRIEF DESCRIPTION OF THE DRAWINGS

The invention will now be further described, by way of example only, and with reference to the accompanying drawings, in which.

DETAILED DESCRIPTION

The storage device of the present invention is required to have a number of key properties. The device must be resistant to the cleaning and sterilisation fluids to which it will be exposed, and must be generally tough and durable. The storage device must protect its contents from damage and as such should be substantially rigid and robust. Finally, the device, while containing the valves or other components, must permit fluids to flow into and out of the device quickly and easily.

Figure 1:
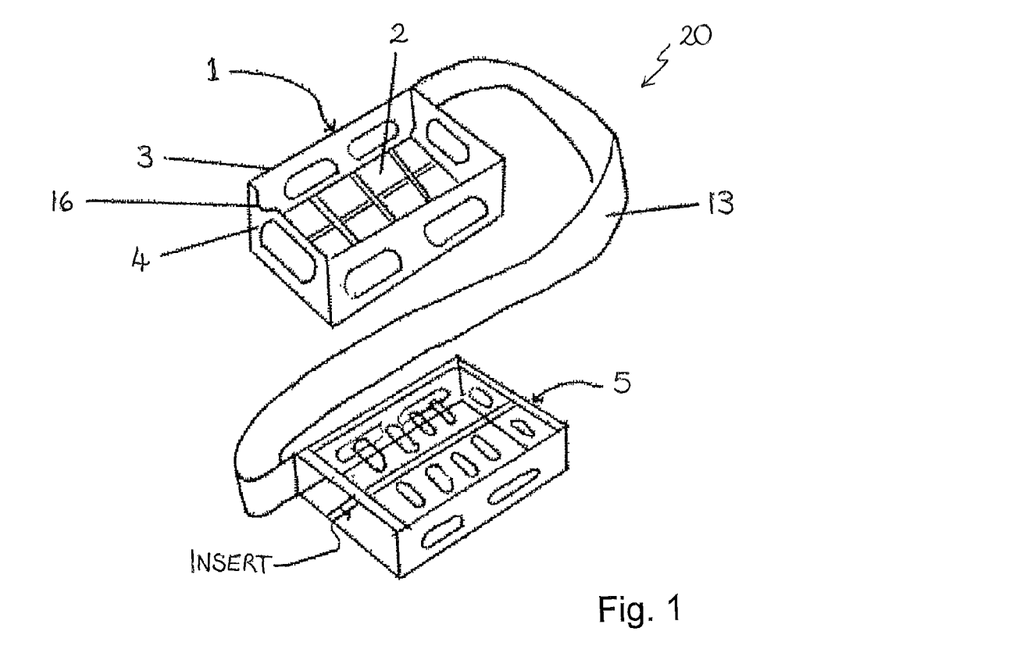
FIG. 1 shows an orthogonal view of a storage device including a tray compartment and sleeve, according to a first embodiment of the present invention, before engagement of the tray compartment with the sleeve.
Figure 3:
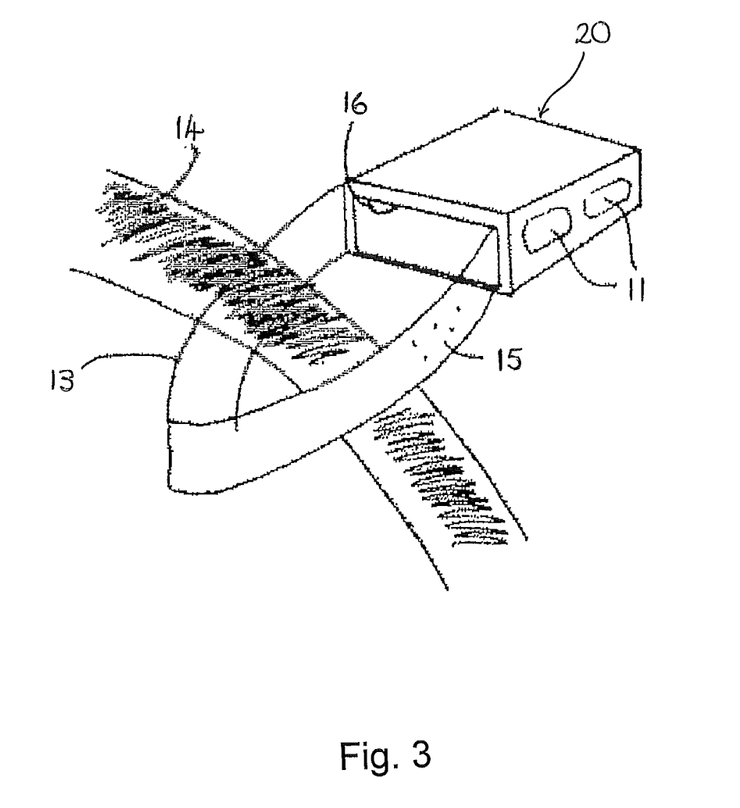
FIG. 3 shows the device of FIGS. 1 and 2 with the tray compartment retained within the sleeve following insertion, with a strap attaching the device around a parent endoscope umbilical cable.

A first embodiment of the storage device 20 is illustrated in FIGS. 1 and 3. In this embodiment, the storage device 20 comprises a tray compartment 1 and a sleeve 5.

Referring first to FIG. 1, the tray compartment 1 is defined by a substantially rectangular base 2 and surrounding side walls 3 and end walls 4 upstanding therefrom on each side. Each wall 3, 4 is, preferably, curved at each end and at the bottom thereof, such that each side wall 3 merges imperceptibly with an adjacent end wall 4, and with the base 2.

The tray compartment 1 is required to be large enough to accommodate various flexible medical endoscope valves of different sizes without undue stress being applied to the valves, yet must at the same time be small enough to fit into a standard automated endoscope reprocessing (AER) machine. Typically, endoscope valves include suction, air/water, biopsy and A/W cleaning valves.

Therefore it is preferred that the side walls 3 along the length of the base ideally have an external length of about 100 mm, whilst the end walls 4 ideally have an external length of about 70 mm. The depth of the tray compartment 1 is ideally about 50 mm.

A sleeve 5 receives the tray compartment 1 through an open end. The sleeve 5 may be closed at the other end, or if it is open, then an end of the tray compartment 1 will act to close it.

The sleeve 5 has internal dimensions which correspond to the external dimensions of the tray compartment 1 to ensure a close fit once assembled together. As an example, the sleeve 5 might have an internal length of about 105 mm, an internal width of about 75 mm and an internal depth of about 55 mm, although these dimensions may vary depending on the thickness of the material that the tray compartment is constructed from.

A strap 13 connects the tray compartment 1 to the sleeve 5, a first end of the strap 13 being attached to a corner of the tray compartment 1 and a second end of the strap 13 being attached to a corner of the sleeve 5.

Figure 2:
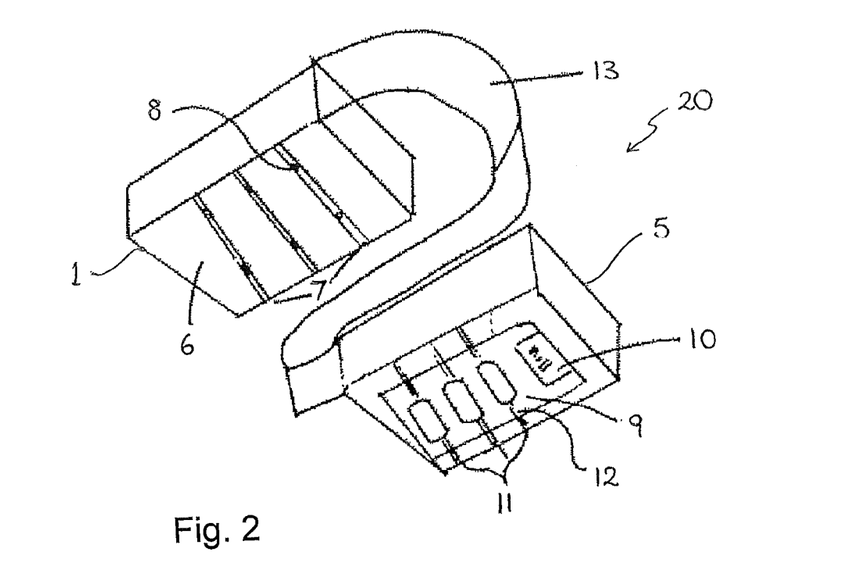
FIG. 2 shows an underside view of the tray compartment and sleeve of FIG. 1, having projections arranged to interlock.

FIG. 2 shows an underside view of FIG. 1, wherein the base of the sleeve 5 has a detachable portion 9 in the form of a tear-off disassembly strip, which can be removed from the sleeve 5 when sufficient force is applied. The detachable portion 9 is, ideally, defined by a perforated edge and, preferably, has a tab 10 extending from one side to facilitate detachment.

The underside 6 of the tray compartment 1 contains a number of struts 7 which extend across the width of the tray compartment 1. Each strut 7 has a number of moulded protrusions 8 provided on it that are arranged to engage with a corresponding number of moulded protrusions 12 provided on a corresponding number of struts 11 on the sleeve 5 when the tray compartment 1 is inserted into the sleeve 5. The protrusions 8, 12 are, preferably, formed as semi-domes and arranged such that, when the tray compartment 1 is inserted into the sleeve 5, the rounded parts of each semi-dome protrusion 8, 12 pass over each other.

However, if an attempt is made to retract the tray compartment 1 once it has been inserted into the sleeve 5, the flat sides of the semi-dome protrusions 8, 12 interlock to prevent the tray compartment 1 from being retracted from the sleeve 5 hence providing a secure storage device.

The struts 11 on the sleeve 5 are arranged on the detachable portion 9 of the sleeve 5, which allows the tray compartment 1 to be released by removing the detachable portion 9 and hence the struts 11 with the protrusions 12 from the sleeve 5. Removal of the detachable portion 9 renders the device unusable for a second time because there are no longer any sleeve protrusions 12 for the tray compartment protrusions 8 to interlock with, thus ensuring the single-use nature of the device.

FIG. 3 shows the sleeve 5 with the tray compartment 1 fully inserted and retained therein. Furthermore, it can be seen that the strap 13 is arranged such that when the tray compartment 1 is fully inserted inside the sleeve 5, the strap 13 can be passed around an endoscope umbilical (light-guide) cable 14 when the tray compartment 1 is being inserted into the sleeve 5 to form a loop that encompasses the endoscope cable 14 so as to ensure that the assembled device remains with the parent endoscope until the detachable portion 9 is detached from the base of the sleeve 5, preferably by means of applying a sufficient force to the tab 10.

The strap 13 has to be long enough to enable the valve tray 1 to be inserted into the sleeve 5 and will therefore ideally be about 15 cm long. The strap 13 has moulded raised projections 15 on both sides to minimise contact between the strap 13 and endoscope cable 14 during a reprocessing procedure.

Both the tray compartment 1 and the sleeve 5 have a plurality of apertures 17 throughout their structures to allow flow of cleaning, disinfection and rinsing solutions during the automated endoscope reprocessing cycle.

When a used endoscope is to be to be cleaned, by placing it into an automated endoscope reprocessor, for example, its valves are removed from the positions on the endoscope and placed in the tray compartment 1.

Often valves will have a chain, or similar, attached with a plastic instruction card on it. Ideally, a groove 16 is provided in a side wall 3 of the tray compartment 1 that is exposed at an end of the sleeve to allow the chain to pass outside of the tray compartment 1 before it is inserted into the sleeve 5, to keep any instruction card outside of the tray compartment 1, where they can be easily accessed.

Once assembled with the strap 13 passing around the endoscope cable 14, the device will ensure that the endoscope valves stay with their parent endoscope during reprocessing of the endoscope and subsequent storage until the endoscope is ready to be used again. At this point retrieval of the endoscope valves can be facilitated by removing the detachable portion 9, thereby allowing the tray compartment 1 to be removed from the sleeve 5. The used tray compartment 1 and sleeve 5 are then discarded and new ones used when the endoscope is next reprocessed.

The present invention has been developed particularly for use in keeping valves as a unique set with flexible medical endoscopes and hence is described herein with particular reference to that use. Nevertheless, it will be appreciated that the present invention may also find use in the safe storage of other medical equipment and/or any other situation where it is important that instrument detachable parts be kept together with the parent item using a single-use product.

It will, of course, be appreciated that other arrangements may be possible according to the present invention. For example, the protrusions 8, 12 may be provided along one or both sides of the tray compartment 1 and sleeve 5, respectively, in which case the detachable portion 9 could be provided on the side(s) of the sleeve 5 to remove the sleeve protrusions 12.

Alternatively, the detachable portion 9 may not be arranged to remove the protrusions 12 from the sleeve 5, but could instead be provided on the top of the sleeve 5, such that its removal will allow the tray compartment 1 to be accessed whilst leaving the securing portions 8. 12 interlocked, thereby ensuring that the device can only be used once.

Furthermore, one of the plurality of protrusions 8, 12 could be substituted by a corresponding number of holes, or slots, provided in the respective struts 7, 11, whereby the semi-dome protrusions can pass into and out of the holes or slots when the tray compartment 1 is being inserted into the sleeve 5, but the flat sides of the protrusions will lock against the flat sides of the holes or slots if any attempt is made to retract the tray compartment 1 from the sleeve 5. Similarly, the plurality of struts could be arranged in a similar semi-dome fashion the length of the strut, such that the flat sides of corresponding struts 7, 11 will interlock. The protrusions could also be staggered on corresponding struts 7, 11 so that there is no interference between protrusions 8, 12 that are not intended to interlock when the tray compartment 1 is being inserted into the sleeve 5.

Another alternative arrangement might be to substitute the sleeve 5 for a lid, which can be arranged to engage with and close the tray compartment 1 using snap-fit securing components, or similar, that are single-use such that disengagement of the lid would only be possible by disabling the securing components used to secure it to the tray compartment 1, or by accessing the tray compartment 1 from above using a detachable portion 9.

Furthermore, the lid may be in the shape of an open box, with sides that extend down from the lid sides, such that when the lid is placed over the tray compartment 1, the sides extend down and over the side walls 3 of the tray compartment 1. Similar to the arrangement discussed above, the protrusions 8, 12, holes/slots, or similar, and detachable portion 9 to remove them, could be provided on the side walls 3 of the tray compartment and lid sides, respectively.

A second preferred embodiment of the present invention is illustrated in FIGS. 4 to 11. In this embodiment a storage device 30 comprises a first, container portion 32 and a second, lid portion 34. A connecting portion or strap 36 connects the container portion 32 to the lid portion 34.

Figure 4:
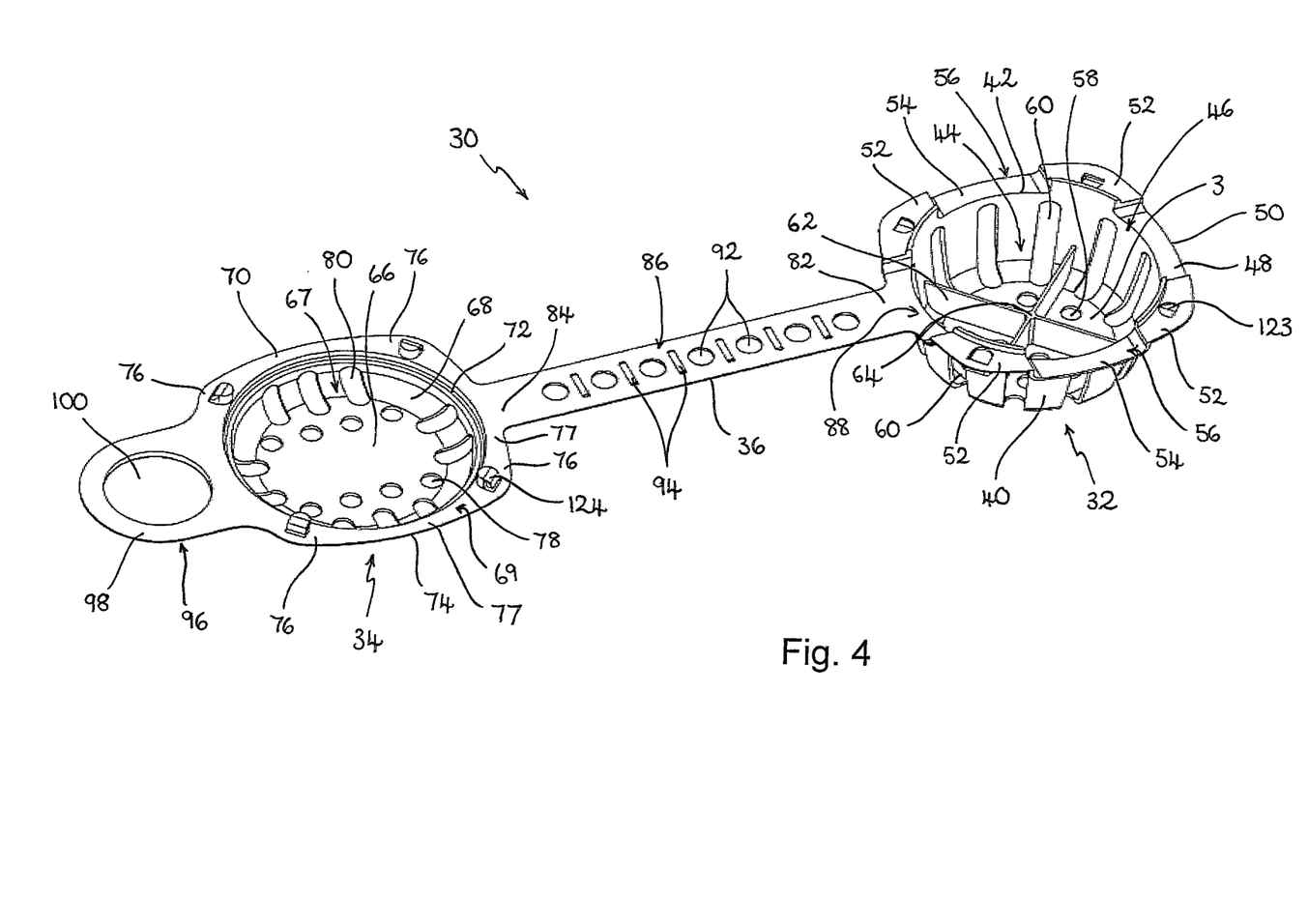
FIG. 4 is a view of a storage device according to a second preferred embodiment of the present invention, the storage device shown in an open configuration before use.

In use, the lid portion 34 engages with the container portion 32 to form an enclosure that surrounds one or more pieces of medical equipment placed within the container portion 32.

The container portion 32 comprises a generally circular base 38 and a side wall 40 that extends from the periphery of the base 38 to a top edge 42 of the container portion 32, thereby defining an interior space 44 and an opening 46 of the container portion 32. A flange or rim 48 extends outwards from the top edge 42 around the complete periphery of the edge 42. Although the top edge 42 is generally circular, an outer edge 50 of the rim 48 is generally square-shaped thereby defining four corner regions 52 of the rim 48.

Regions of the side wall 40 terminating at the corner regions 52 of the rim 48 are of a greater height than regions of the side wall 40 between the corner regions 52. In this way, the corner regions 52 of the rim 48 are raised compared to side regions 54 of the rim 48, between the corner regions 52, and, as such, four dips or recesses 56 are created in the rim 48 between the corner regions 52.

A plurality of holes 58 are formed in the base 38 of the container portion 32, and preferably the holes 58 are spaced evenly over the full area of the base 38. The side wall 40 comprises a plurality of elongate apertures 60 that extend from proximate the base 38 to proximate the top edge 42 and which are spaced evenly around the side wall 40.

The container portion 32 further includes partitioning members 62 that extend across the base 38 of the container portion 32 to divide the base 38 into distinct areas. In this example the partitioning members 62 comprise walls 62 that extend from a central point 64 out to the side wall 40 of the container portion 32. There are four partition walls 62 that are arranged in a cross-shape, thereby dividing the base 38 into four equal sized areas, and the height of the walls 62 is less than half the height of the side wall 40 of the container portion 32. It will be appreciated that, in other embodiments, the container portion 32 may not include partitioning members, or may include less than or more than four partitioning members. Furthermore, the partitioning members may be of any suitable form and may divide the base of the container portion into uneven or irregularly sized areas.

Figure 6:
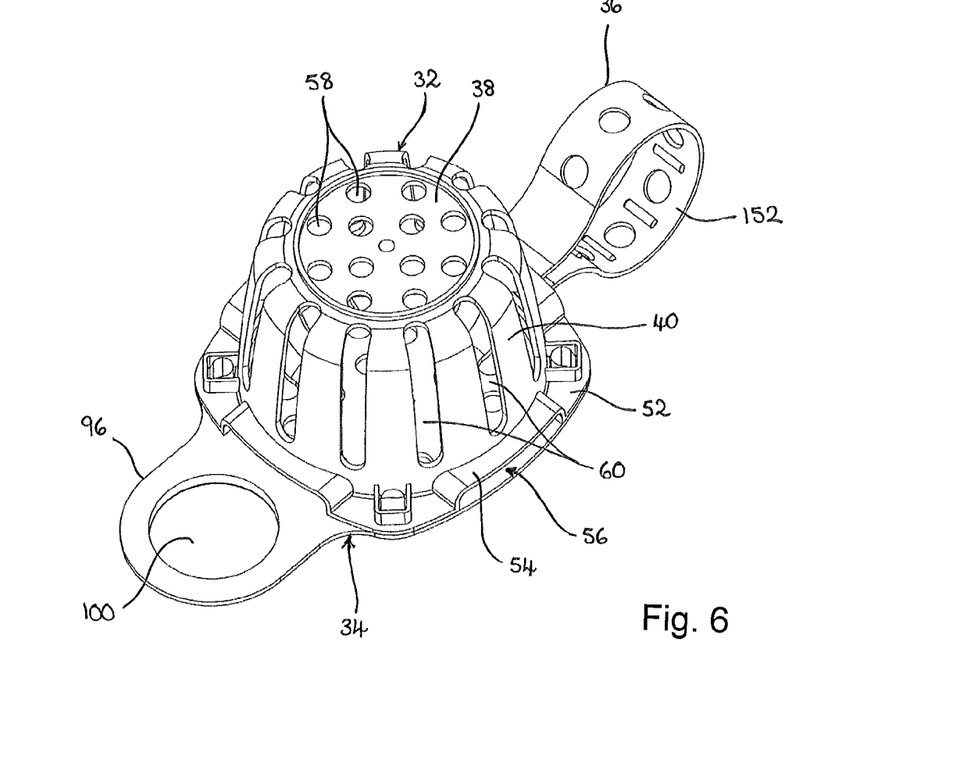
FIG. 6 is a perspective view from underneath the storage device of FIG. 5.

Preferably, the base 38 of the container portion 32 includes a ridge 65 extending from the underside, or exterior, surface of the container portion 32. In use, the device 30 may be stood on the ridge 65 so that fluid is still able to drain from the holes 58 in the base 38.

The lid portion 34 comprises a generally circular central section 66 and a side wall 68 extending around the central section 66, thereby defining a recessed space 67 in the underside 69 of the lid 34. A rim 70 extends outwards from a top edge 72 of the side wall 68. An outer edge 74 of the rim 70 is generally square-shaped thereby defining four corner regions 76 of the rim 70. The dimensions of the lid portion 34 correspond to the dimensions of the container portion 32, and in particular the dimensions of the rim 70 are substantially the same as the dimensions of the rim 48.

A plurality of holes 78 are formed in the central section 66 of the lid portion 34, and a plurality of elongate apertures 80 are formed in the side wall 68 extending from the central section 66 to the top edge 72.

The strap 36 is connected at a first end 82 to the rim 48 of the container portion 32 and at a second end 84 to the rim 70 of the lid portion 34. The width of the strap 36 is substantially less than a width of the container portion 32, and in this example, the strap 36 extends from a side region 54 of the rim 48 to a first side region 77 of the rim 70. The strap 36 is flexible, and in this embodiment, the thickness of the strap 36 is the same as the thickness of both the rims 48, 70, and a first side 86 of the strap 36 is integral or flush with a top surface 88 of the rim 48 and an underside surface 69 of the rim 70.

The strap 36 comprises a plurality of holes 92 spaced along the length of the strap 36. A plurality of ribs 94 extend across the width of the strap 36 on the first side 86 of the strap 36 and each one of the plurality of ribs 94 is located between two holes 92. The ribs 94 do not extend across the full width of the strap in this example, but in other embodiments the ribs may extend for the full width of the strap and there may be fewer or more ribs than holes.

A handle portion or grip portion 96 extends from a second side region 77 of the rim 70, opposite to the first side region 77. The handle portion 96 comprises a tab 98 formed from a planar sheet having the same thickness as the rim 70. The tab 98 includes a centrally positioned hole 100, through which a user of the device may place one or more fingers as will be described below.

The device 30 further comprises securing means 122, the first part 123 of the securing means 122 being located on the container portion 32 and a second part 124 of the securing means 122 being located on the lid portion 34, as shown most clearly in FIGS. 7-10.

Figure 7:
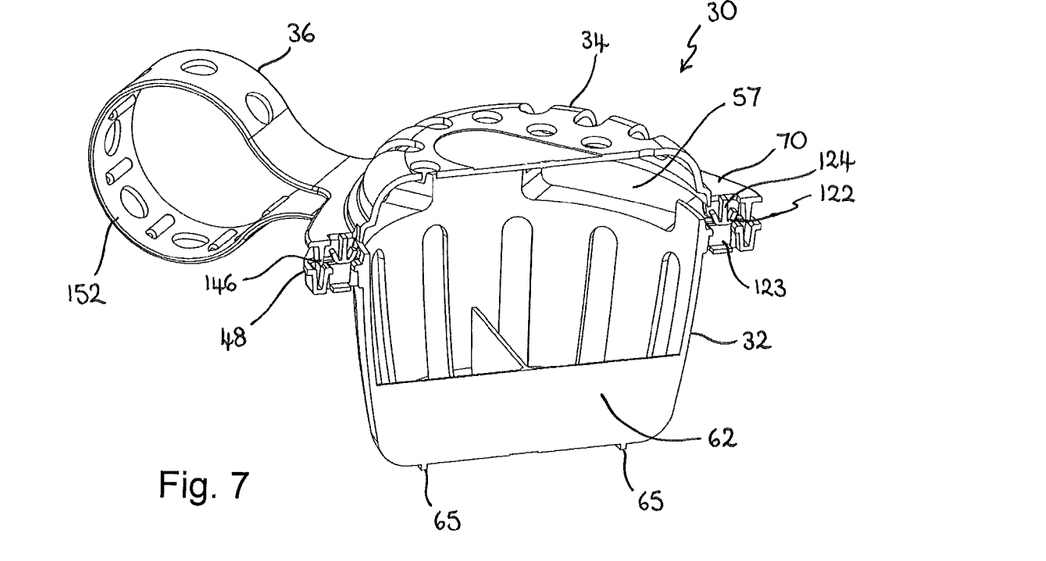
FIG. 7 is a cross-sectional view through the storage device of FIG. 5 in a partially open configuration, before securing means are engaged.
Figure 8:
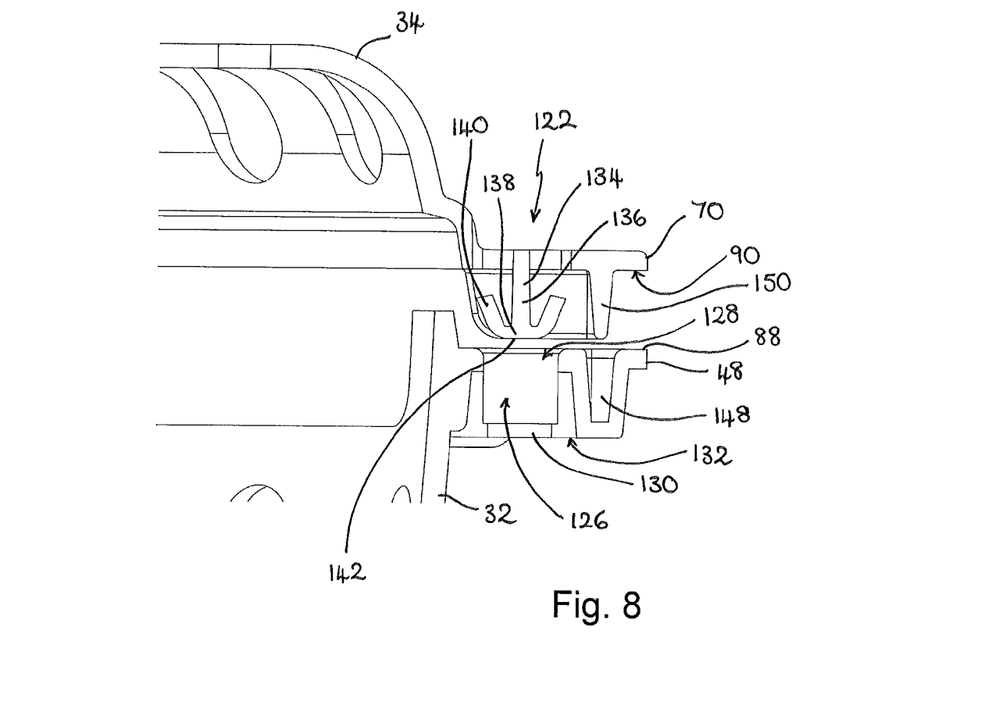
FIG. 8 is a detailed view of the securing means of FIG. 7.

The first part 123 of the securing means 122 comprises a cavity 126 formed in the rim 48. The cavity 126 has an opening 128 in the top surface 88 of the rim 48, for receiving the second part 124 of the securing means 122. Apart from the opening 128, the cavity 126 is substantially enclosed, and in particular, a base 130 of the cavity 126 is formed by a part of the undesired surface 132 of the rim 48.

The second part 124 of the securing means 122 comprises a locking member 134 projecting substantially perpendicularly from the underside surface 90 of the rim 70. The locking member 134 comprises a stem portion 136 and a head portion 138. The head portion 138 comprises two arms or barbs 140 that extend outwards and rearwards from the distal end 142 of the locking member 134. In this way, the barbs 140 extend back towards the underside surface 90 on the rim 70. The distance between the ends 144 of the barbs 140 is greater than the width of the opening 128 of the first part 123 of the securing means 122, such that deflection of the barbs 140 is required to insert the locking member 134 into the cavity 126.

Figure 9:
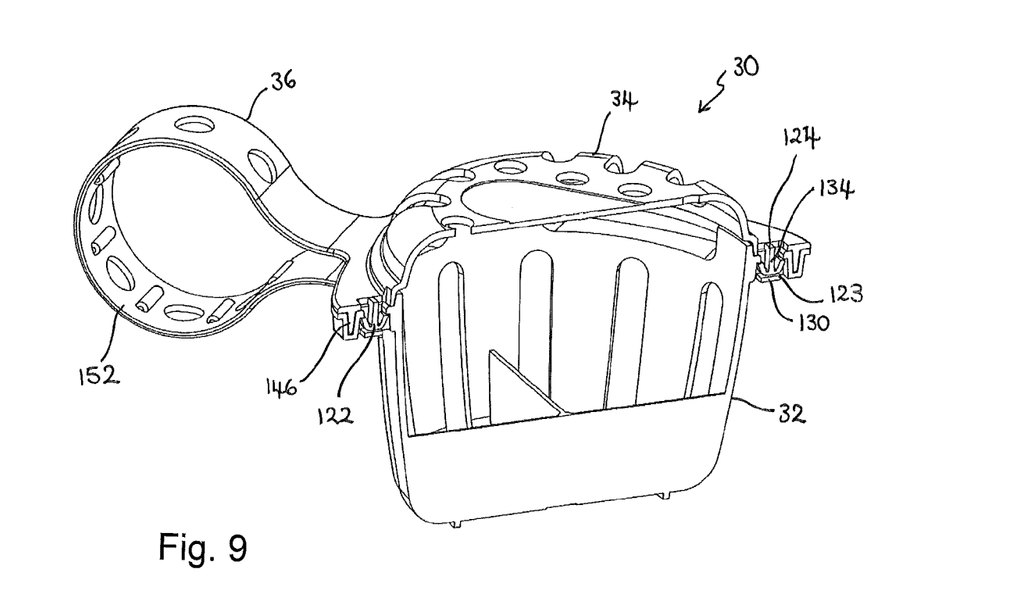
FIG. 9 is a cross-sectional view through the storage device of FIG. 5 in a fully closed configuration, with the securing means engaged.
Figure 10:
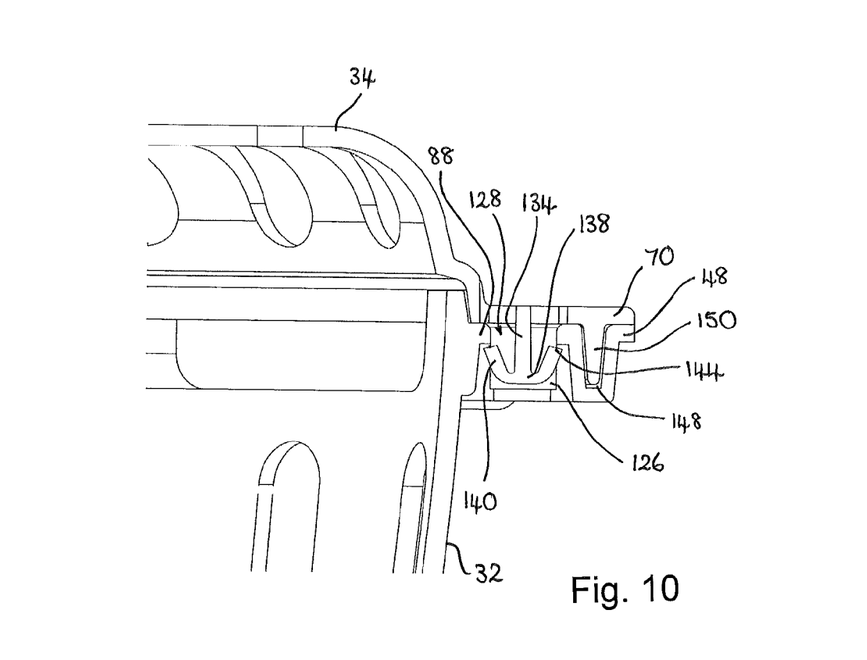
FIG. 10 is a detailed view of the securing means of FIG. 9.

FIGS. 9 and 10 show the storage device 30 in a closed configuration in which the first and second parts 123, 124 of the securing means 122 are fully engaged. In this position, the head portion 138 of the locking member 134 is fully received within the cavity 126. The ends 144 of the barbs 140 are located behind part of the top surface 88 of the rim 48 surrounding the opening 128. In this way, once the first and second parts 123, 124 of the securing means 122 have been fully engaged it is not possible to withdraw the locking member 134 from the cavity 126 due to the presence of the barbs 140.

In this embodiment the storage device 30 comprises four securing means 122, one of the securing means 122 being located in each corner region 52, 76 of the rims 48, 70.

The storage device 30 may also comprise additional engaging means 146 to aid in the alignment and sealing of the lid portion 34 with the container portion 32. In this example, the engaging means 146 comprises a recess 148 formed in the rim 48 of the container portion 32 and a protrusion 150 extending from the rim 70 of the lid portion 34. The recess 148 and the protrusion 150 are arranged such that the protrusion 150 is received within the recess 148 when the lid portion 34 is aligned with and secured over the container portion 32. In this embodiment, the engaging means 146 comprises four recesses 148 located adjacent to the cavities 126 in the corner regions 52 of the rim 48 and four protrusions 150 located adjacent to the locking members 134 in each of the four corner regions 76 of the rim 70.

Returning to FIG. 4, this view shows the device 30 in an open configuration before use. In use, a user of the device 30 places the required valves or other components (not shown) into the interior space 44 of the container portion 32. For example, four endoscope valves may be placed in the container portion 32, one in each of the areas bounded by the partitioning walls 62.

Figure 5:
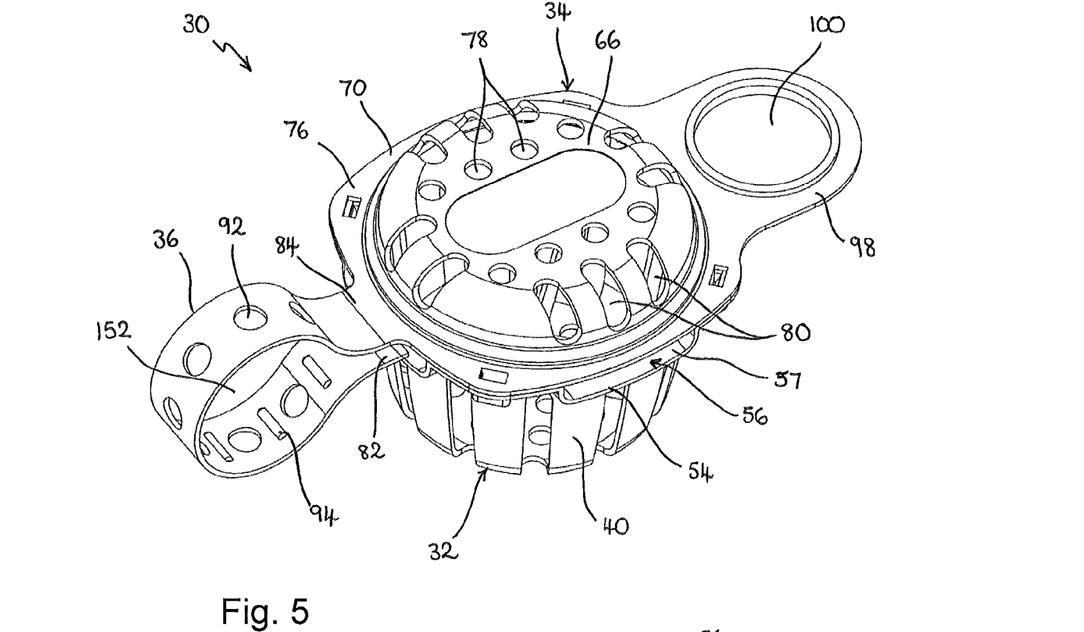
FIG. 5 is a perspective view from the top of the storage device of FIG. 4 in a closed configuration.

The device 30 is then closed by bending the strap 36 around the parent endoscope and placing the lid 34 over the opening 46 of the container portion 32, as shown in FIG. 5. The rims 48, 70 are aligned using the engaging means 146 and are pressed together so that the locking members 134 are pushed through the openings 128. In particular, as the lid 34 of the device 30 is closed, the resilient barbs 140 of the head portion 138 of each locking member 134 deforms slightly as it is pushed through the respective opening 128. The barbs 140 then return to their original shape once through the opening 128 such that the head portion 138 of the locking member 134 is retained within the cavity 126.

In this position, the top surfaces 88 of the corner regions 52 of the rim 48 are in contact with the underside surface 69 of the corner regions 76 of the rim 70. The recesses 56 mean that the lower side regions 54 of the rim 48 are not in contact with the respective side regions 77 of the rim 70 and, as such, the recesses 56 form additional openings 57 between the interior space 44 of the container portion 32 and the surroundings.

As described previously, some valves will typically have an instruction or record card attached to them by means of a chain or similar. When the valves are placed in the container portion 32 of the present embodiment of the device 30, the chains or other attachment means may be laid within the recess 56, so that, when the device 30 is closed, the chains or similar pass out of the container portion 32 through the openings 57 so that the instruction or record cards remain on the outside of the device 30 for ease of access at all times.

In order to retain the device 30 with the parent endoscope (not shown), or other piece of medical equipment, the strap 36 is wrapped around a portion of the parent endoscope as the device 30 is closed. In this way, the portion of the parent endoscope is contained within a closed loop 152 of the strap 36. The ribs 94 on the strap 36 are located on the inner surface of the loop 152 and act to minimise the contact of the strap 36 with the parent endoscope.

During sterilisation of the valves or components within the device 30, the plurality of holes and apertures 56, 60, 78, 80 both in the container portion 32 and the lid portion 34 allow fluid to flow into and out of the interior space 44 of the device 30. The greater the number of holes and apertures 56, 60, 78, 80 the more easily the cleaning and sterilisation fluids are able to flow through the device 30 to reach the valves. However, the number of holes and apertures 56, 60, 78, 80 should not be too great, such that the rigidity and robustness of the container portion 32 and lid portion 34 are affected, thereby compromising the protective nature of the storage device 30.

When a user wishes to remove the valves or components from the container portion 32, he or she grips the container portion 32 of the device 30 and pulls the handle portion 96 of the lid portion 34. Preferably the user inserts one or more fingers through the hole 100 in the tab 98 in order to apply sufficient force to pull the lid portion 34 away from the container portion 32.

Because the barbs 140 cannot be pulled back through the openings 128, the force the user applies to the lid portion 34 breaks the slender stem portions 136 of each of the locking members 134. The lid portion 34 can then be pulled away from the container portion 32, the strap 36 can be unwrapped from the parent endoscope, and the valves or components removed from the container portion 32.

Because the cavities 126 are substantially enclosed, the head portions 138 of the locking members 134 remain within the cavities 126 when the device 30 is opened.

Of importance is the fact that once the storage device 30 has been used and opened once, the breaking of the locking members 134 means that the device 30 cannot be reused and must be disposed of. This reduces the likelihood of cross-contamination of the medical equipment.

Figure 11:
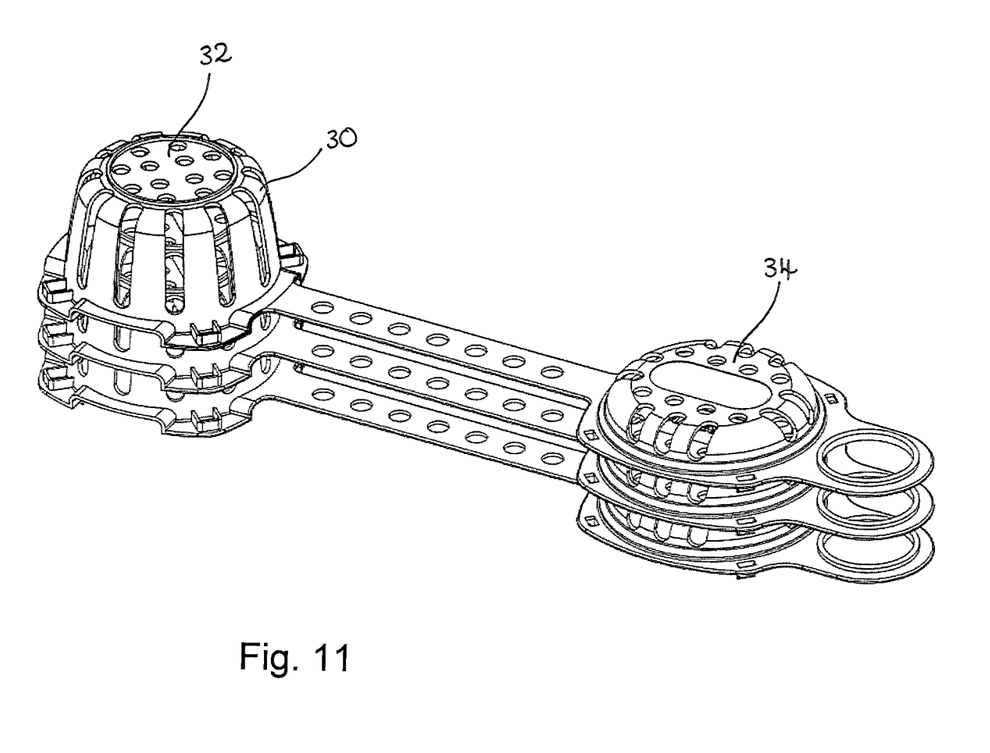
FIG. 11 is a view of three storage devices of FIG. 4, showing the devices stacked for storage and transportation.

FIG. 11 shows three storage devices 30 stacked for the purposes of transportation and storage. The design of the storage device 30 means that the container portions 32 and lid portions 34 of the devices 30 nest together such that each storage device 30 only takes up a minimal amount of space.

The storage device 30 of the present invention, therefore, overcomes many of the problems associated with current storage devices. In particular, the present invention provides a single use storage device that allows valves and other components to be kept with a parent endoscope or other piece of medical equipment during storage, cleaning and sterilisation.

The invention claimed is:

1. A single-use storage device for retaining endoscope valves with an endoscope, the storage device being resistant to cleaning and sterilization fluids, and the storage device comprising: a container portion configured to hold one or more endoscope valves; a closure portion, designed to engage with the container portion to form an enclosure around said endoscope valves; a plurality of apertures permitting fluid flow through the storage device; securing means to secure the closure portion to the container portion, the securing means arranged such that once the closure portion has been secured to the container portion using the securing means the closure portion and container portion cannot be separated without permanently disabling the securing means; and a connecting portion joining the container portion to the closure portion, the connecting portion comprising a flexible, elongate strap having a first end and a second end, the first end being attached to the container portion and the second end being attached to the closure portion, and the strap being arranged such that, in use, when the closure portion is secured to the container portion the elongate strap forms a loop around a part of said endoscope, the strap having a circular loop shape with a majority of the loop protruding away from the container portion and closure portion; the container portion includes a rim and the closure portion includes a rim, and wherein in use, when the closure portion is secured to the container portion, one or more openings are formed between said rim of the container portion and said rim of the closure portion.

2. A single-use storage device as claimed in claim 1, wherein the strap includes one or more protrusions on a first surface, the protrusions being on an inner surface of the loop when the closure portion is secured to the container portion.

3. A single-use storage device as claimed in claim 1, wherein the container portion and the closure portion include a plurality of apertures.

4. A single-use storage device as claimed in claim 1, wherein a first part of the securing means is provided in the container portion and a second part of the securing means is provided in the closure portion.

5. A single-use storage device as claimed in claim 1, where disabling the securing means includes breaking a part of the securing means.

6. A single-use storage device as claimed in claim 1, wherein the closure portion includes a handle portion, arranged to enable a user to grip said handle to separate the closure portion from the container portion.

7. A single-use storage device as claimed in claim 1, wherein the securing means comprises an opening in the container portion and a protrusion in the closure portion, and wherein a part of the protrusion is passed through the opening to secure the closure portion to the container portion.

8. A single-use storage device as claimed in claim 7, wherein the securing means comprises more than one opening and more than one protrusion.

9. A single-use storage device as claimed in claim 1, wherein the container portion includes a partitioning member.

10. A single-use storage device as claimed in claim 1, wherein the closure portion is a lid.

11. A single-use storage device as claimed in claim 1, wherein the container portion is a tray compartment.

12. A single-use storage device as claimed in claim 1, wherein the container portion is a tray compartment and the closure portion is a sleeve, and the tray compartment is receivable within the sleeve.

13. A single-use storage device as claimed in claim 12, wherein a first part of the securing means is provided on the tray compartment and a second part of the securing means is provided on the sleeve.

14. A single-use storage device as claimed in claim 13, wherein said first and second parts of the securing means are a plurality of semi-dome protrusions arranged such that when the tray compartment is engaged with the sleeve flat surfaces of said protrusions interlock to prevent disengagement of the tray compartment from the sleeve.

15. A single-use storage device as claimed in claim 1, wherein the container portion and closure portion are formed from a plastics material.

16. A single-use storage device for retaining a first piece of medical equipment together with a second piece of medical equipment during cleaning and/or storage, the storage, device being resistant to cleaning and sterilization fluids, and the storage device comprising: a container portion, configured to hold said first piece of medical equipment; a closure portion, designed to engage with the container portion to form an enclosure around said first piece of medical equipment; a plurality of apertures permitting fluid flow through the storage device; securing means to secure the closure portion to the container portion, the securing means arranged such that once the closure portion has been secured to the container portion using the securing means the closure portion and the container portion cannot be separated without permanently disabling the securing means; and a connecting portion joining the container portion to the closure portion, the connecting portion comprising a flexible, elongate strap having a first end and a second end, the first end being attached to the container portion and the second end being attached to the closure portion, and the strap being arranged such that, in use, when the closure portion is secured to the container portion the elongate strap forms a loop around a part of said second piece of medical equipment, the strap having a circular loop shape with a majority of the loop protruding away from the container portion and closure portion; the container portion includes a rim and the closure portion includes a rim, and wherein in use, when the closure portion is secured to the container portion, one or more openings are formed between said rim of the container portion and said rim of the closure portion.

17. A single-use storage device as claimed in claim 1, wherein the container portion, closure portion and connecting portion are integrally formed.

* * * * *